(12) United States Patent
Kanomi et al.

(10) Patent No.: US 6,354,834 B2
(45) Date of Patent: Mar. 12, 2002

(54) ORTHODONTIC SUPPORTING STRUCTURE

(75) Inventors: Ryuzo Kanomi, Himeji; Katsuyuki Nakagawa, Otawara; Yoshiharu Shin, Tokyo-to, all of (JP)

(73) Assignee: Sankin Kogyo Kabushiki Kaisha, Tochigi-ken (JP)

( * ) Notice: Subject to any disclaimer, the term of this patent is extended or adjusted under 35 U.S.C. 154(b) by 0 days.

(21) Appl. No.: 09/740,195

(22) Filed: Dec. 18, 2000

(30) Foreign Application Priority Data

Dec. 28, 1999 (JP) ............................................. 11-375204

(51) Int. Cl.7 ................................................. A61C 3/00
(52) U.S. Cl. ......................................... 433/18; 433/173
(58) Field of Search .............................. 433/18 OR, 17, 433/173

(56) References Cited

U.S. PATENT DOCUMENTS

| | | | | |
|---|---|---|---|---|
| 5,066,224 A | * | 11/1991 | Block et al. | 433/18 |
| 5,938,437 A | * | 8/1999 | De Vincenzo | 433/18 |
| 5,967,772 A | * | 10/1999 | Gray | 433/18 |
| 6,193,509 B1 | * | 2/2000 | De Vincenzo | 433/18 |

* cited by examiner

Primary Examiner—John J. Wilson
(74) Attorney, Agent, or Firm—Jordan and Hamburg LLP

(57) ABSTRACT

An orthodontic supporting structure of the present invention comprises an implant unit which is implantable in a jaw bone and a connecting unit which includes an arm part having a fastening portion. The implant unit has a narrow part in its upper portion. The connecting unit further includes an engaging part having an opening at one end. The engaging part fits on the narrow part of the implant unit. The connecting unit can be attached to the implant unit in a simple way by sliding the engaging part along the narrow part and then crimping far ends of the engaging part.

18 Claims, 13 Drawing Sheets

ORTHODONTIC SUPPORTING STRUCTURE

BACKGROUND OF THE INVENTION

1. Field of the Invention

The present invention relates to supports for correcting abnormal dentition which can serve as supporting points for relocating or moving an improperly positioned tooth in orthodontic treatment.

2. Description of the Related Art

Orthodontic treatment for correcting irregularities in teeth arrangement, such as crowded teeth, reversed occlusion or inclination of front teeth to the labial side, is getting popular.

One of the most popular methods of orthodontic treatment includes the steps of fixing brackets to surfaces of individual teeth with an adhesive, for instance, passing an arch wire through the brackets, and relatively moving the individual teeth by applying external forces (which may be hereinafter referred to as correcting forces in this Specification), such as pushing, pulling or twisting forces, to the teeth by use of a restoring force caused by the elasticity of the arch wire, so that the teeth would be adjusted to take proper positions and directions to achieve as a whole a correct dentition. This method may be hereinafter referred to as relative movement orthodontic treatment.

In such relative movement orthodontic treatment, molars, especially the first molars, which are large and difficult to move, are used as sources of anchorage in most cases. It is, however, too much to say that the molars do not move at all. In fact, the molars which have been located at correct positions could be displaced in certain cases as a result of orthodontic treatment. On the contrary, there are cases where it is desired to positively move a molar. In such cases, the orthodontic treatment involves complicated movements and techniques for correcting the arrangement of the teeth which would require an extended period of time, imposing a heavy burden on a patient.

Another method of relative movement orthodontic treatment is to use extraoral anchorage in which the head of a patient is used as a source of anchorage, for instance. An extraoral anchorage orthodontic appliance, however, imposes considerable mental pain and stress on the patient because wearing the extraoral anchorage appliance greatly affects his or her daily life.

In addition, the aforementioned method of relative movement orthodontic treatment is not suited for correcting the position of a single tooth.

To overcome the foregoing problems, U.S. Pat. No. 5,921,774 (Japanese Unexamined Patent Publication No. 10-99347) proposes orthodontic treatment using an orthodontic supporting structure.

This orthodontic supporting structure comprises an implant portion (implant unit) to be implanted in a desired site in a jaw bone and an exposed portion (connecting unit) which can be attached to a head of the implant portion. The implant portion measures 2 mm at the maximum in the diameter of its horizontal cross section and the exposed portion includes an arm having a hook (fastening part) which would extend into the oral cavity.

With the support implanted in the jaw bone, one end of a resin chain or a metallic coil spring or the like is connected to the fastening part of the support and the other end is connected to a bracket or a lingual button, for instance, which is fixed to a tooth in order to apply a correcting force, such as a pushing or pulling force, to the tooth.

Since the arm of the orthodontic supporting structure allows the fastening part serving as a supporting point for the correcting force to be located away from the implant site in the jaw bone, it is possible to situate the fastening part at a position most preferable for applying the correcting force even when the support is implanted where it does not interfere with nerves or tooth roots.

The orthodontic supporting structure of the aforementioned Publication is suited for correcting the position of a single tooth because it can apply the correcting force directly to each individual tooth. Furthermore, this orthodontic supporting structure makes it possible to exert the correcting force from a supporting point most suited to the tooth to be corrected without adversely affecting correctly positioned teeth. Thus, the support can correct the improperly positioned tooth without the need for complicated orthodontic treatment and reduce the time period required for the treatment.

SUMMARY OF THE INVENTION

An orthodontic supporting structure of the present invention comprises an implant unit which is implanted in a desired site in a jaw bone and a connecting unit attachable to an upper portion of the implant unit, the connecting unit including an arm part having a fastening portion which extends in an oral cavity and an engaging part having an opening at one end which is formed to allow the connecting unit to detachably fit on the implant unit in a direction intersecting a longitudinal axis of the implant unit.

These and other objects, features and advantages of the present invention will become more apparent upon a reading of the following detailed description along with the accompanying drawings.

DESCRIPTION OF THE PREFERRED EMBODIMENTS

Figure 1A:
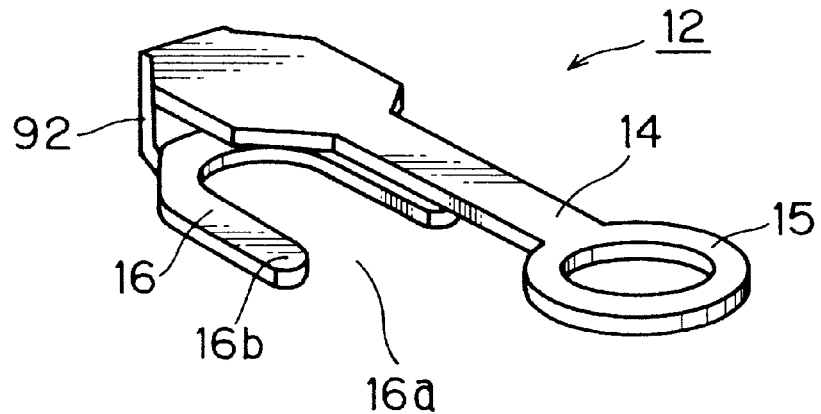
FIG. 1A is a perspective view of a connecting unit of an orthodontic supporting structure according to a first embodiment of the invention.

Orthodontic treatment is performed in an oral cavity which provides only a limited treatment space and requires the use of such treatment appliances as an extremely small orthodontic supporting structure (whose implant unit measures 1.2 mm in the diameter of the horizontal cross section, for instance). Therefore, the treatment is difficult to perform and requires an orthodontist to have a high level of treatment skill. For this reason, there has been the need for easier-to-use treatment appliances.

Accordingly, it is an object of the invention to provide orthodontic supporting structures which allow easier handling and operation.

An orthodontic supporting structure of the invention comprises an implant unit which is implanted in a desired site in a jaw bone and a connecting unit attachable to an upper portion of the implant unit, the connecting unit including an arm which extends in an oral cavity and has a fastening part and an engaging part having an opening at one end which is formed to allow the connecting unit to detachably fit on the implant unit in a direction intersecting a longitudinal axis of the implant unit.

If the orthodontic supporting structure is of a type in which the implant unit and the connecting unit are fixed by a screw, the screw is necessarily an extremely small one which is considerably difficult to handle in the narrow space of the oral cavity. If a handle of a screwdriver used for turning the screw is to be directed toward a cheek, for example, it would be even more difficult to turn the screw.

In contrast, the connecting unit can be easily attached to the implant unit by just sliding the connecting unit in a horizontal direction toward the upper portion of the implant unit in the present invention. This is because the orthodontic supporting structure of the invention is constructed such that the connecting unit can fit on the implant unit in the direction intersecting the longitudinal axis of the implant unit as stated above.

In this invention, the aforementioned horizontal direction (or the direction intersecting the longitudinal axis of the implant unit) is preferably a direction generally perpendicular to the longitudinal axis of the implant unit.

This is because the implant unit is usually implanted generally at right angles to a gingival surface, the direction generally perpendicular to the longitudinal axis of the implant unit is almost parallel to the gingival surface, and therefore, it is possible to avoid interference with the cheek or lips if the connecting unit is slid almost parallel to the gingival surface.

Preferably, the orthodontic supporting structure of the invention should be constructed such that the implant unit has a narrow part in the upper portion and the engaging part of the connecting unit has a U-shaped inner surface structure which can fit on the narrow part of the implant unit.

In this construction, the narrow part of the implant unit fits into the opening in the U-shaped inner surface structure of the engaging part when the connecting unit and the implant unit are mated. In addition, this construction prohibits the connecting unit from coming off upward from the implant unit because a head of the implant unit is thicker than the narrow part. Here, it is to be noted that the direction in which the implant unit is implanted may be regarded as a downward direction and its opposite direction may be regarded as an upward direction in the present specification.

In another preferred form of the invention, a locking mechanism is provided at a point of contact between the implant unit and the connecting unit to prevent the connecting unit from turning about the implant unit.

When the connecting unit is mated with the implant unit, the extending direction of the arm is fixed as the locking mechanism prevents the connecting unit from turning about the implant unit. It is therefore possible to maintain the fastening part at a desired position.

In still another preferred form of the invention, the arm of the connecting unit and the engaging part thereof which is shorter than the arm are joined by an intermediate part to together form a continuous J-shaped structure, the intermediate part having a flat area at least in part of its inner surface, a head of the implant unit just above the narrow part has a polygonal cross section or a generally circular or elliptical cross section with its side cut to form a flat surface, and the flat area on the inner surface of the intermediate part comes in contact with the flat surface of the head when the connecting unit is mated with the implant unit. The aforementioned locking mechanism is formed of the flat area on the inner surface of the intermediate part of the connecting unit and the flat surface of the head of the implant unit.

In this construction, the connecting unit is prohibited from turning about the implant unit when the former is mated with the latter, because the flat area on the inner surface of the intermediate part of the connecting unit comes in contact with the flat surface of the head (any one side of the head if it has a polygonal shape).

In yet another preferred form of the invention, the narrow part of the implant unit has a polygonal cross section, an elliptical cross section or a generally circular cross section with its side cut to form a flat surface, and the engaging part of the connecting unit has a polygonal inner surface structure, an elliptical inner surface structure or a generally circular inner surface structure with its side cut to form a flat surface such that the engaging part can fit on the narrow part. In other words, both the narrow part and the engaging part have a polygonal surface structure, an elliptical surface structure or a generally circular surface structure with its side cut to form a flat surface, and the engaging part can fit on the narrow part in this preferred form of the invention. The aforementioned locking mechanism is formed of the cross-sectional shape of the narrow part and the inner surface structure of the engaging part. The engaging part having such an inner surface structure of course has the opening at one end.

In this construction, the connecting unit is firmly fixed to the implant unit and is prohibited from turning in a reliable fashion as the narrow part of the implant unit properly fits into the engaging part.

Preferably, at least the engaging part of the connecting unit is made of a plastically deformable material and the engaging part is fixed to the narrow part of the implant unit by crimping the engaging part. A typical example of such plastically deformable material is metal, such as stainless steel, titanium, a titanium alloy or an alloy of cobalt and titanium.

The connecting unit can be firmly fixed to the implant unit by crimping the engaging part as stated above.

If the engaging part is not crimped, the connecting unit may come off the implant unit when a force is applied to the connecting unit in a direction opposite to the direction in which the connecting unit is slid when fitting it to the implant unit. If the engaging part is crimped as stated above, the connecting unit would not come off even when such a force is applied thereto. Even if the engaging part is not crimped, however, the connecting unit would not come off if the force is applied in a direction within about 90° on either side (180° sector area as a whole) of the direction in which the connecting unit is slid when fitting it to the implant unit.

If the engaging part is not crimped as stated above, the connecting unit can be easily removed from the implant unit. This would make it easier to replace a wire or the like attached to the fastening part or to alter the direction of traction exerted on a tooth midway during orthodontic treatment.

In another preferred form of the invention, at least the engaging part of the connecting unit is made of a plastically deformable material and the width of the opening in the engaging part is smaller than the maximum thickness of a part of the implant unit where the engaging part is fitted.

If the opening in the engaging part is slightly smaller than the part of the implant unit (e.g., the aforementioned narrow part) where the engaging part is fitted, the edge of the opening in the engaging part will come in contact with the part of the implant unit and produce resistance when the connecting unit is slid in the horizontal direction. If the connecting unit is forcibly pushed further in the same direction, the plastically deformable engaging part will easily deform, allowing the connecting unit to slide into position. The engaging part restores its original shape at this point and mates the implant unit and the connecting unit. In this construction, the engaging part would not come off easily even when a force is exerted on the connecting unit in a direction opposite to the direction in which the connecting unit was slid.

As a correcting force exerted on a tooth is usually 100 to 300 g (980 to 2940 mN), and is 1 kg at the maximum, the engaging part should preferably be made of a material capable of just withstanding such correcting forces exerted in the direction opposite to the direction in which the connecting unit was slid. A typical example of such plastically deformable material is metal, such as stainless steel, titanium, a titanium alloy or an alloy of cobalt and titanium.

If it is desired to remove the connecting unit from the implant unit, the connecting unit should be pulled in the direction opposite to the direction in which the connecting unit was slid. The pulling force will cause the engaging part to deform, allowing the implant unit to slip off from the engaging part. The pulling force should be just as large as to cause the engaging part to deform overwhelming the aforementioned correcting force.

In the orthodontic supporting structure of this preferred form the connecting unit can be easily attached to and removed from the implant unit. This would make it easier to replace a wire or the like attached to the fastening part or to alter the direction of traction exerted on a tooth midway during orthodontic treatment by once removing the fastening part.

In another preferred form of the invention, a projection is formed in an inner surface of the engaging part of the connecting unit and a recess which can fit on the projection is formed on the implant unit. In this construction, the projection on the engaging part fits into the recess in the narrow part when the connecting unit and the implant unit are mated. As a result, the connecting unit and the implant unit are fixed more securely and, therefore, the connecting unit will not come off easily from the implant unit.

In a further preferred form of the invention, the arm of the connecting unit is made of a plastically deformable material.

Since the arm can be bent in a desired angular or curved shape in this preferred form, it is possible to adjust the bend of the arm to locate the fastening part at a desired position even after the connecting unit has been firmly attached to the implant unit. According to the invention, the orthodontic supporting structure may be constructed such that the arm can be bent in either the horizontal direction or vertical direction (parallel to the longitudinal axis of the implant unit).

As a correcting force exerted on a tooth is 1 kg at the maximum as stated earlier, the engaging part should preferably be made of a material capable of just withstanding such correcting forces after its plastic deformation.

Furthermore, it is preferable that an embedded portion of the implant unit be not larger than 2 mm in diameter and that the embedded portion of the implant unit be externally threaded.

First Embodiment

Figure 1B:
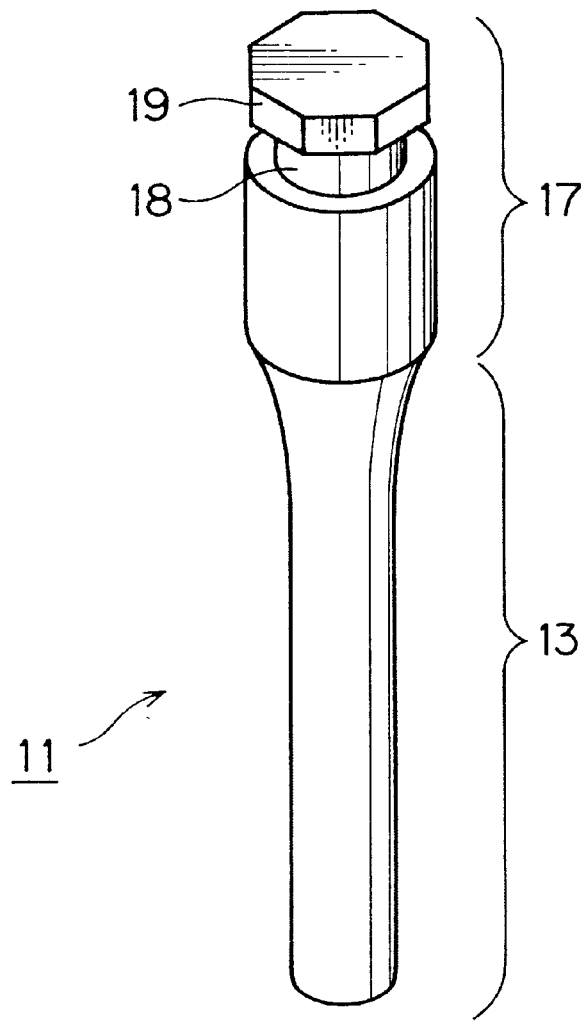
FIG. 1B is a perspective view of an implant unit of the support according to the first embodiment.
Figure 2A:
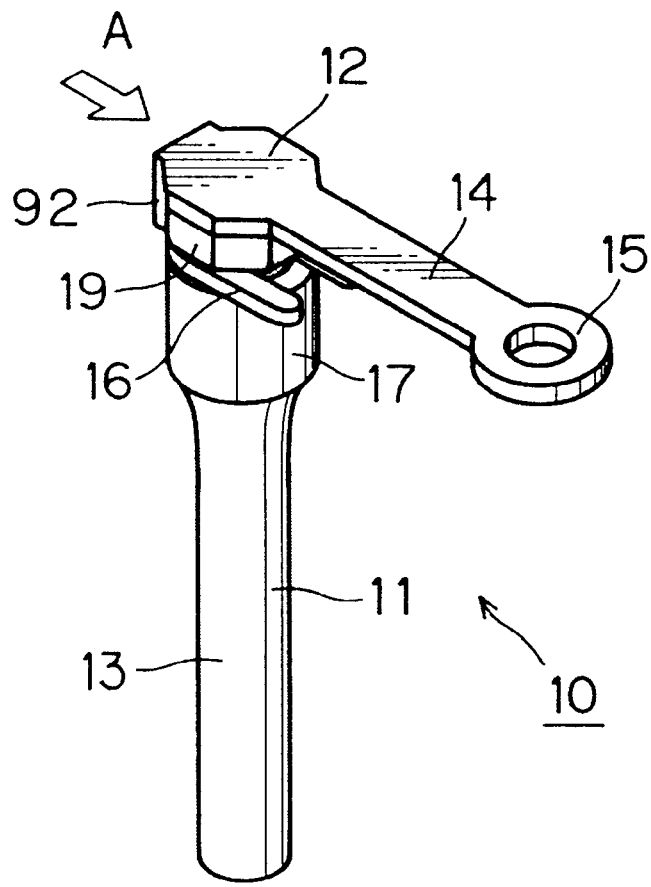
FIGS. 2A and 2B are diagrams illustrating how the connecting unit of the first embodiment is fitted to the implant unit.
Figure 2B:
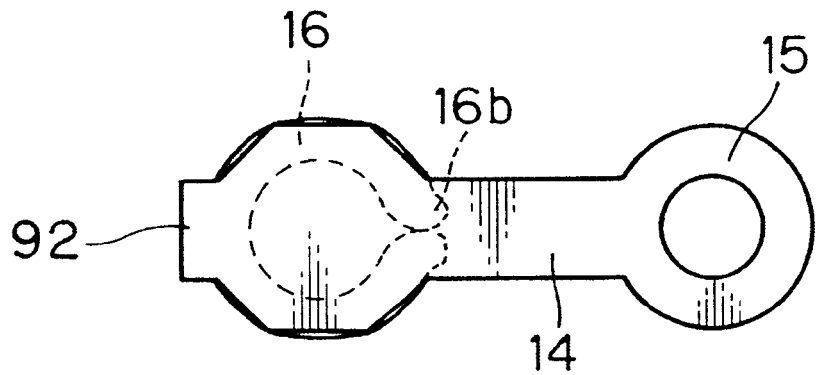

FIGS. 1A and 1B illustrate an orthodontic supporting structure 10 according to a first embodiment of the invention, in which FIG. 1A is a perspective view showing a connecting unit 12 of the support 10 and FIG. 1B is a perspective view showing an implant unit 11 of the support 10. FIGS. 2A and 2B are diagrams illustrating how the connecting unit 12 is fitted to the implant unit 11, in which FIG. 2A is a perspective view showing a situation where the connecting unit 12 is just being fitted to the implant unit 11 and FIG. 2B is a perspective view showing a situation where their assembly has been completed.

The implant unit 11 includes an upper portion 17 which is exposed to the oral cavity and an embedded portion 13 which is embedded in a jaw bone, wherein a narrow part 18 is formed in the upper portion 17. A head 19 of the upper portion 17 just above the narrow part 18 is shaped into a regular octagon in top view.

The connecting unit 12 includes an arm 14 which extends into the oral cavity with a ring-shaped fastening part 15 provided at a far end of the arm 14. The connecting unit 12 further includes an engaging part 16 having a U-shaped inner surface structure of which size is appropriate to fit on the narrow part 18 of the upper portion 17. The arm 14 and the engaging part 16 joined by an intermediate part 92 having a flat inner surface together form a continuous J-shaped structure. The connecting unit 12 is made of a plastically deformable material, such as stainless steel, titanium, a titanium alloy or an alloy of cobalt and titanium.

To attach the connecting unit 12 to the implant unit 11, an opening 16a in the engaging part 16 is aligned with the narrow part 18 of the implant unit 11 and the connecting unit 12 is pushed in the direction of arrow A shown in FIG. 2A until one of side surfaces of the head 19 of the implant unit 11 comes into contact with the flat inner surface of the intermediate part 92. Far ends 16b of the engaging part 16 are then crimped as shown in FIG. 2B to complete assembly of the implant unit 11 and the connecting unit 12.

Since the flat inner surface of the intermediate part 92 and one flat side surface of the head 19 are in close contact as stated above, the connecting unit 12 is prohibited from turning about the implant unit 11. Furthermore, since the far ends 16b of the engaging part 16 are crimped as stated above, the connecting unit 12 would not easily come off even when a force is applied to the connecting unit 12 in a direction opposite to the direction of the arrow A. Moreover, the connecting unit 12 is prevented from coming off upward because it is held in position by the head 19 which is thicker than, or horizontally extends beyond, the narrow part 18.

The orthodontic supporting structure 10 can be assembled by simple operation, just involving the steps of sliding the connecting unit 12 in a horizontal direction shown by the arrow A and then crimping (or mechanically bending) the far ends 16b of the engaging part 16 to fix the connecting unit 12 to the implant unit 11 as stated above. This assembly operation can be easily carried out even in a limited space like the oral cavity, so that the orthodontic supporting structure 10 of this embodiment provides ease of handling. Yet the connecting unit 12 can be firmly fixed to the implant unit 11.

An operational procedure for performing orthodontic treatment using the orthodontic supporting structure 10 is as follows. First, an orthodontist implants the implant unit 11 in a desired site in a jaw bone and waits until the embedded portion 13 of the implant unit 11 is firmly set in the jaw bone. Then, the connecting unit 12 is fitted and fixed to the implant unit 11 by the method described above. When fitting the connecting unit 12 to the implant unit 11, the extending direction of the arm 14 can be changed in steps of 45° about the center of the implant site, because the head 19 of the implant unit 11 has a regular octagonal cross section.

Subsequently, one end of a rubber ring, a resin chain or a metallic coil spring or the like is hooked to the fastening part 15 and the other end is connected to a bracket or a lingual button, for instance, which is fixed to a tooth as in the conventional fashion to thereby apply a correcting force to the tooth.

If it is desired to alter the direction of traction exerted on the tooth during the treatment, it would be necessary to undo the crimped far ends 16b of the engaging part 16, detach the connecting unit 12 from the implant unit 11 and attach the former to the latter again in a proper position. According to the present embodiment, it is possible to adjust the direction of traction by repositioning the connecting unit 12 leaving the implant unit 11 as it is. This method of orthodontic treatment is preferable in that it allows adjustment of the orthodontic supporting structure 10 without causing surgical damage to the jaw bone, whenever such adjustment is needed.

Second Embodiment

Figure 3A:
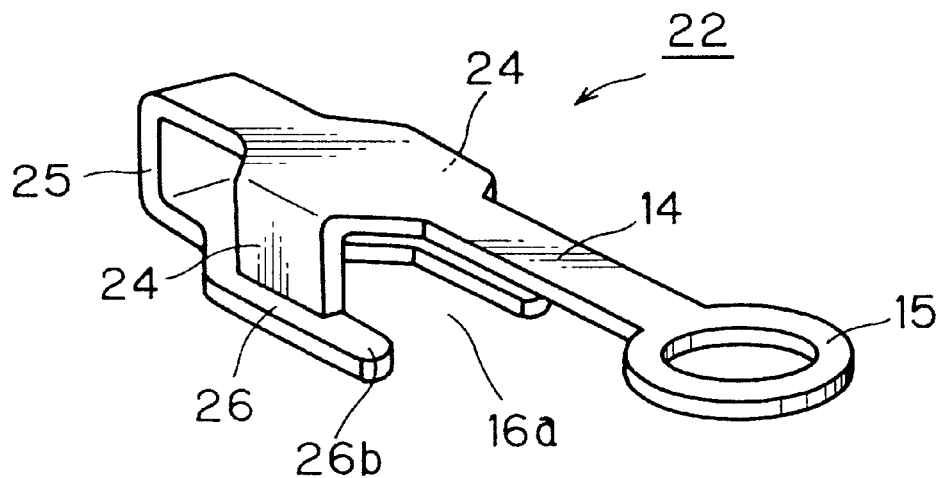
FIG. 3A is a perspective view showing a connecting unit of an orthodontic supporting structure according to a second embodiment of the invention.
Figure 3B:
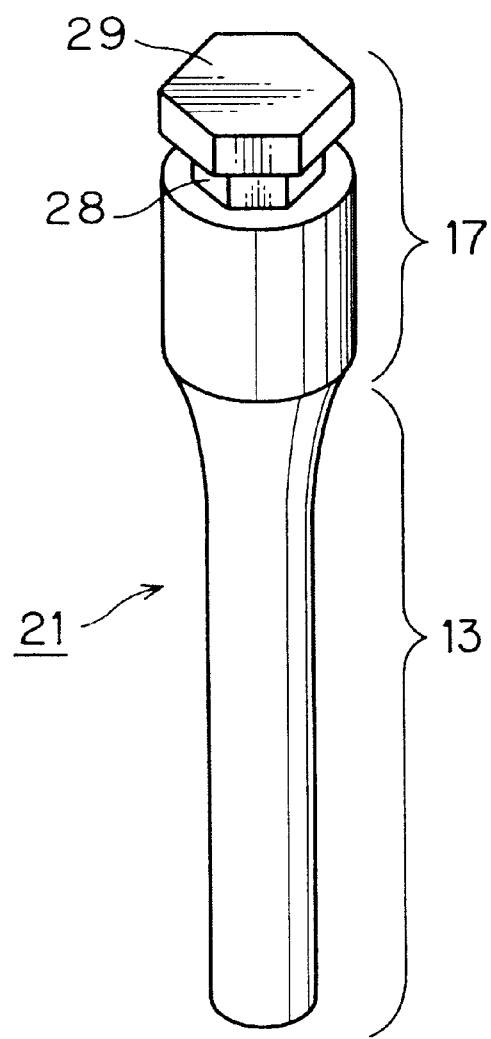
FIG. 3B is a perspective view of an implant unit of the support according to the second embodiment.
Figure 4:
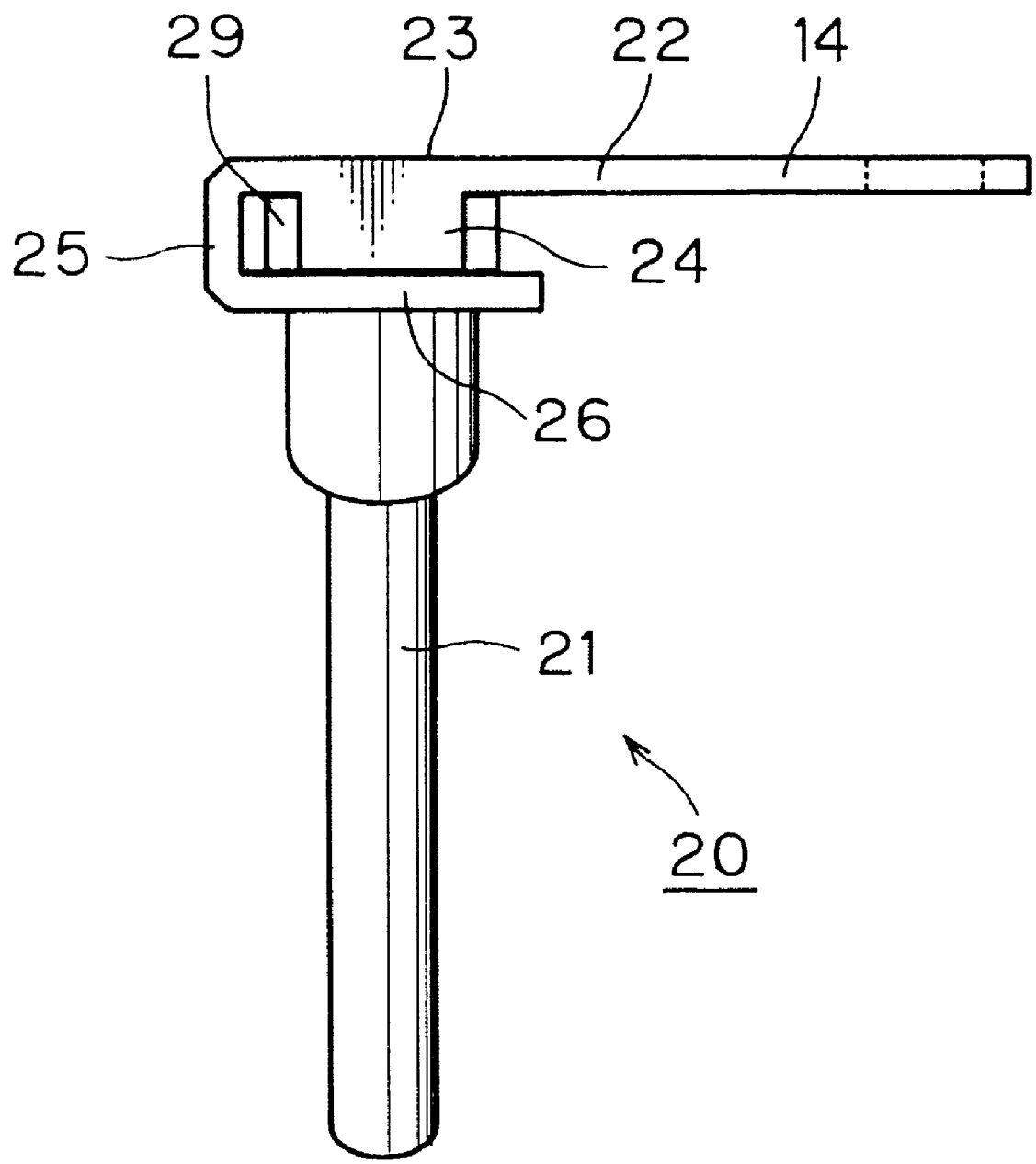
FIG. 4 is a front view illustrating how the connecting unit of the second embodiment is fitted to the implant unit.

FIGS. 3A–3B and 4 illustrate an orthodontic supporting structure 20 according to a second embodiment of the invention, in which FIG. 3A is a perspective view showing a connecting unit 22 of the support 20, FIG. 3B is a perspective view showing an implant unit 21 of the support 20, and FIG. 4 is a front view showing how the connecting unit 22 is fitted to the implant unit 21.

In this embodiment, a narrow part 28 of the implant unit 21 is shaped into a regular hexagon in top view as is a head 29 of an upper portion 17 of the implant unit 21.

An engaging part 26 of the connecting unit 22 has an opening 16a at one end. This opening 16a has a generally hexagonal inner surface structure having four sides and opening at one end, so that the inner shape of the opening 16a is appropriate to fit on the narrow part 28 of the implant unit 21. The connecting unit 22 has a pair of side flaps 24 extending downward from two opposite sides of a top plate part 23 which goes into contact with the head 29 of the implant unit 21, so that inner surfaces of the side flaps 24 come in contact with side surfaces of the head 29 when the connecting unit 22 is fitted to the implant unit 21. An arm 14 and the engaging part 26 of the connecting unit 22 joined by an intermediate part 25 together form a continuous J-shaped structure. The connecting unit 22 is made of a plastically deformable material, such as stainless steel or titanium. In FIGS. 3A, 3B and 4, elements identical or equivalent to those shown in FIGS. 1A–1B and 2 are designated by the same reference numerals and a description of such elements is omitted.

To assemble the orthodontic supporting structure 20, the opening 16a in the engaging part 26 of the connecting unit 22 is aligned with the narrow part 28 of the implant unit 21 and the connecting unit 22 is pushed until its engaging part 26 fits on the narrow part 28. At this point, the two side flaps 24 of the connecting unit 22 fit over two side surfaces of the head 29. Since the narrow part 28 has a regular hexagonal cross section like the head 29 and the engaging part 26 of the connecting unit 22 is constructed into a corresponding shape in this embodiment, the extending direction of the arm 14 can be adjusted in steps of 60° when fitting the connecting unit 22 to the implant unit 21. Far ends 26b of the engaging part 26 are then crimped to complete assembly as shown in FIG. 4.

Since the engaging part 26 fits on the narrow part 28 of the implant unit 21 and the side flaps 24 fit over the head 29 as described above, the connecting unit 22 is prohibited from turning about implant unit 21. Furthermore, since the far ends 26b of the engaging part 26 are crimped as stated above, the connecting unit 22 would not easily come off the implant unit 21. Moreover, the connecting unit 22 is prevented from coming off upward because it is held in position by the head 29 which is thicker than, or horizontally extends beyond the narrow part 28, so that the connecting unit 22 is firmly fixed to the implant unit 21.

Third Embodiment

Figure 5A:
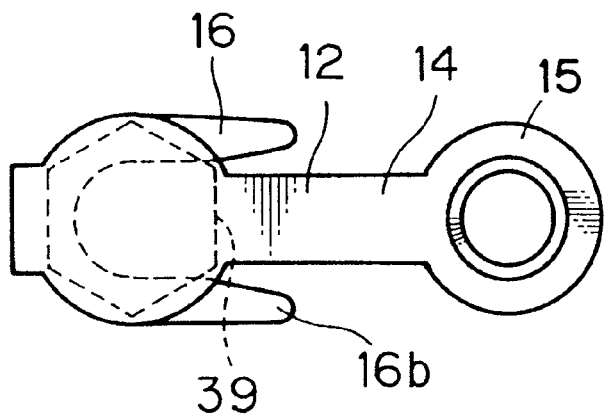
FIG. 5A is a top view of an orthodontic supporting structure according to a third embodiment of the invention.
Figure 5B:
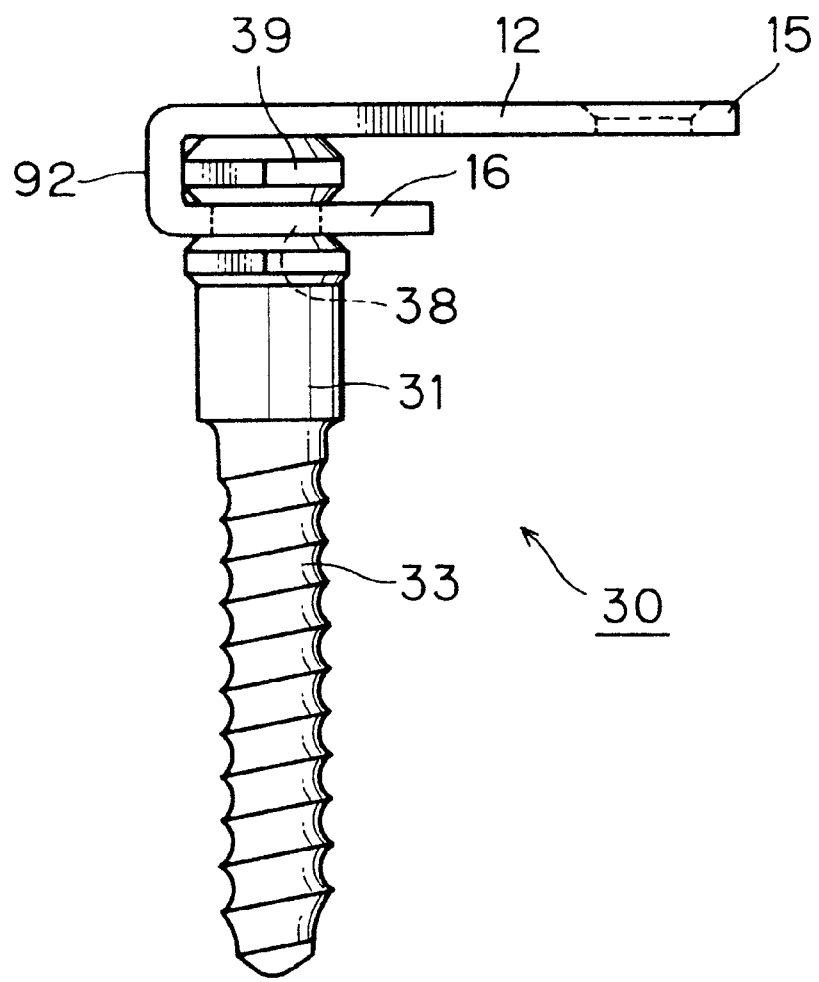
FIG. 5B is a side view of the orthodontic supporting structure according to the third embodiment.

FIGS. 5A–5B are diagrams showing an orthodontic supporting structure 30 according to a third embodiment of the invention, in which FIG. 5A is a top view and FIG. 5B is a side view. In FIGS. 5A–5B, elements identical or equivalent to those shown in FIGS. 1A–1B and 2 are designated by the same reference numerals and a description of such elements is omitted.

In this embodiment, an embedded portion 33 of an implant unit 31 is externally threaded. A middle part of a head 39 of the implant unit 31 has a hexagonal cross section in top view with upper and lower parts of the head 39 tapering off from the middle part as illustrated. A narrow part 38 of the implant unit 31 has a circular cross section in top view. An engaging part 16 of a connecting unit 12 has an opening 16a at one end and this opening 16a has a semicircular inner surface structure which fits over the narrow part 38 of the implant unit 31.

The orthodontic supporting structure 30 of the third embodiment allows an orthodontist to easily implant the implant unit 31 by screwing it into a jaw bone. Since the middle part of the head 39 has a hexagonal cross section, a wrench may be used when implanting the implant unit 31, further facilitating implanting operation.

Furthermore, since the head 39 of the implant unit 31 is tapered downward, the engaging part 16 of the connecting unit 12 can be smoothly fitted onto the narrow part 38 of the implant unit 31.

Since an intermediate part 92 of the connecting unit 12 and one flat side surface of the head 39 come in close contact with each other in this embodiment as in the first embodiment, the connecting unit 12 is prohibited from turning about the implant unit 31.

Although far ends 16b of the engaging part 16 are not crimped in FIGS. 5A–5B, the far ends 16b may be crimped to fix the connecting unit 12 to the implant unit 31 more firmly.

Furthermore, this embodiment makes it easier to pass a resin chain, for instance, through a hole in a fastening part 15 of an arm 14 because the hole is countersunk as depicted in FIG. 5B.

Fourth Embodiment

Figure 6A:
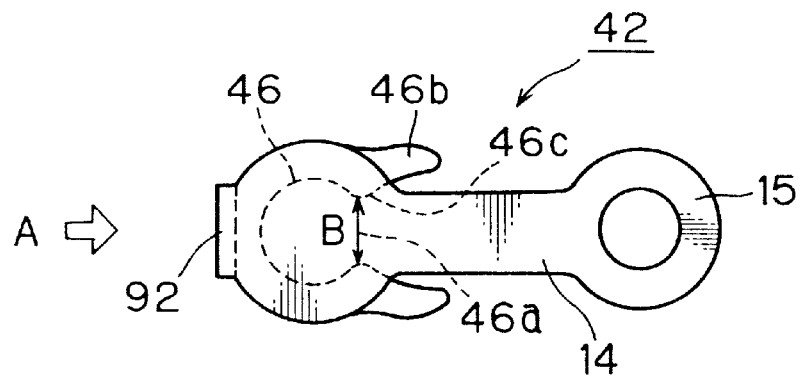
FIG. 6A is a top view of a connecting unit of an orthodontic supporting structure according to a fourth embodiment of the invention.
Figure 6B:
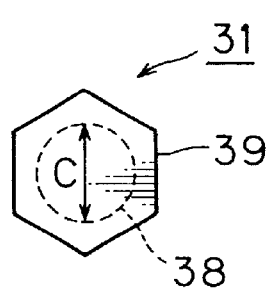
FIG. 6B is a top view of an implant unit according to the fourth embodiment.
Figure 6C:
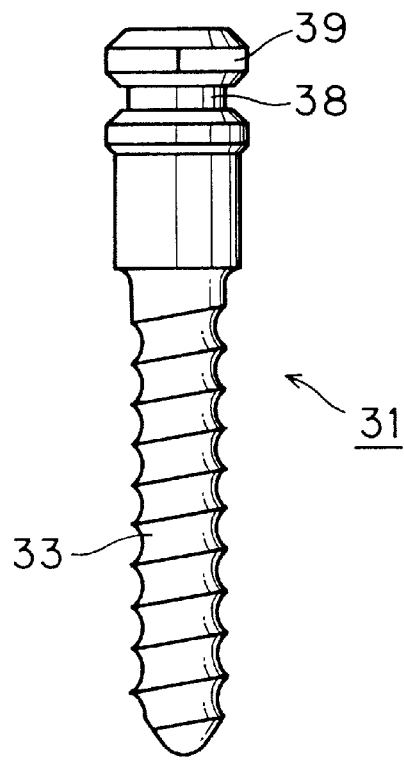
FIG. 6C is a side view of the implant unit according to the fourth embodiment.

FIGS. 6A–6C are diagrams showing an orthodontic supporting structure 40 according to a fourth embodiment of the invention, in which FIG. 6A is a top view of a connecting unit 42 of the support 40, FIG. 6B is a top view of an implant unit 31 of the support 40, and FIG. 6C is a side view of the implant unit 31. In FIGS. 6A–6C, elements identical or equivalent to those shown in FIGS. 1A–1B, 2 and 5A–5B are designated by the same reference numerals and a description of such elements is omitted.

In this embodiment, the implant unit 31 has a narrow part 38 having a circular cross section in top view as well as a head 39 having a hexagonal cross section in top view. An engaging part 46 and an arm 14 of the connecting unit 42 joined by an intermediate part 92 together form a continuous J-shaped structure. The intermediate part 92 has a flat inner surface which comes in contact with one side surface of the head 39.

The engaging part 46 forms a C-shaped circular arc which fits on the narrow part 38 of the implant unit 31. The width B of a constricted part of an opening 46a in the engaging part 46 is made smaller than the diameter C of the narrow part 38. The constricted part of the opening 46a is formed by projections 46c from both sides of the engaging part 46. Two far ends 46b of the engaging part 46 extending beyond the constricted part fan out as depicted in FIG. 6A.

The connecting unit 42 is made of a plastically deformable material, such as stainless steel, titanium or a titanium alloy.

To attach the connecting unit 42 to the implant unit 31, the engaging part 46 of the connecting unit 42 is aligned with the narrow part 38 of the implant unit 31 and the connecting unit 42 is slid in the direction of arrow A. Since the far ends 46b of the engaging part 46 fan out as stated above, the narrow part 38 is smoothly guided into the engaging part 46 until the narrow part 38 comes in contact with the projections 46c. If the connecting unit 42 is forcibly pushed further in the direction of arrow A, the engaging part 46 deforms, or spreads outward, allowing the narrow part 38 to pass between the projections 46c and completely fit in the engaging part 46. Since the engaging part 46 restores its original shape at this point, the narrow part 38 of the implant unit 31 is prohibited from coming off the engaging part 46.

Furthermore, since one side surface of the head 39 is held in close contact with the inner surface of the intermediate part 92 as in the foregoing embodiments, the connecting unit 42 is prohibited from turning about the implant unit 31.

The connecting unit 42 is firmly fixed to the implant unit 31 in this fashion.

Fifth Embodiment

Figure 7A:
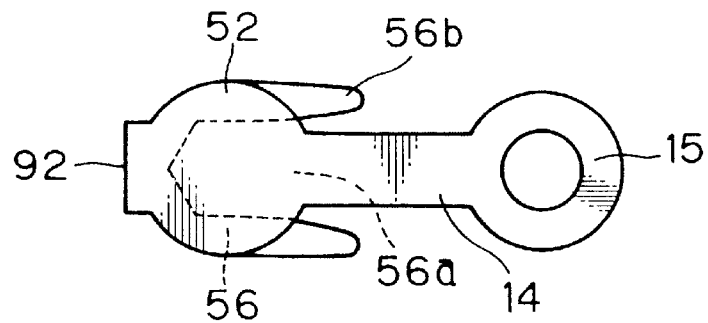
FIG. 7A is a top view of a connecting unit of an orthodontic supporting structure according to a fifth embodiment of the invention.
Figure 7B:
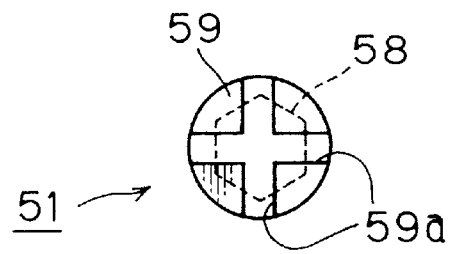
FIG. 7B is a top view of an implant unit according to the fifth embodiment.
Figure 7C:
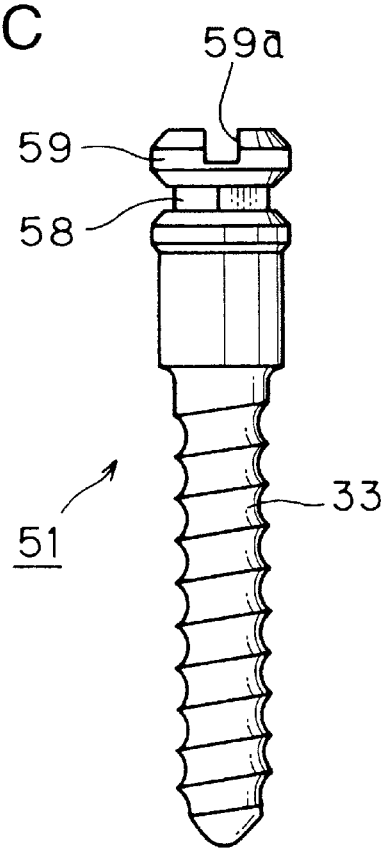
FIG. 7C is a side view of the implant unit according to the fifth embodiment.

FIGS. 7A–7C are diagrams showing an orthodontic supporting structure 50 according to a fifth embodiment of the invention, in which FIG. 7A is a top view of a connecting unit 52 of the support 50, FIG. 7B is a top view of an implant unit 51 of the support 50, and FIG. 7C is a side view of the implant unit 51. In FIGS. 7A–7C, elements identical or equivalent to those shown in FIGS. 1A–1B, 2, 5A–5B and 6A–6C are designated by the same reference numerals and a description of such elements is omitted.

In this embodiment, a narrow part 58 of the implant unit 51 has a hexagonal cross section in top view while a head 59 of the implant unit 51 has a circular cross section in top view. As shown in FIG. 7B, a cross-shaped recess 59a (intersecting slots) is formed in a top surface of the head 59.

An engaging part 56 of the connecting unit 52 has an opening 56a at one end. This opening 56a has a generally hexagonal inner surface structure having four sides and opening at one end, so that the inner shape of the opening 56a is appropriate to fit on the narrow part 58 of the implant unit 51.

To attach the connecting unit 52 to the implant unit 51, the connecting unit 52 is slid in a horizontal direction so that the narrow part 58 of the implant unit 51 slips into the opening 56a in the engaging part 56 as in the foregoing embodiments. After fitting the engaging part 56 to the narrow part 58 of the implant unit 51 in this way, far ends 56b of the engaging part 56 are crimped to fix the connecting unit 52 in position.

Furthermore, since there is formed the cross-shaped recess 59a in the top surface of the head 59 in this embodiment, an orthodontist may implant the implant unit 51 in a jaw bone by screwing it with a screwdriver, for example.

Sixth Embodiment

Figure 8A:
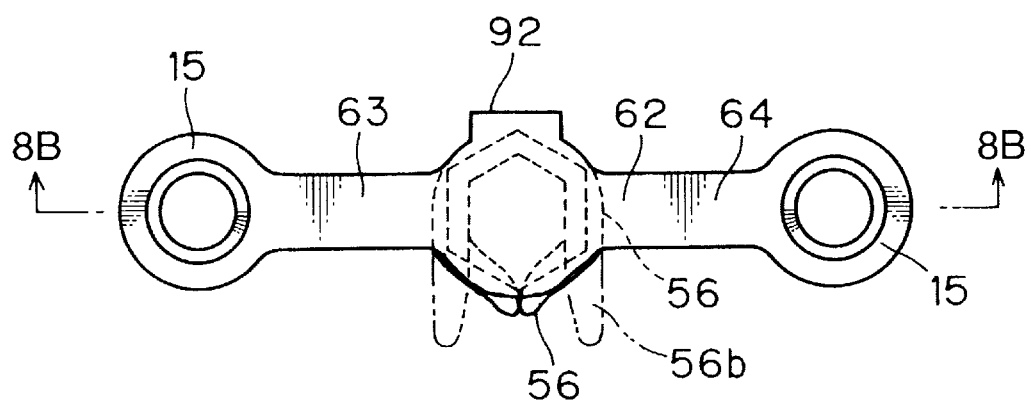
FIG. 8A is a top view of an orthodontic supporting structure according to a sixth embodiment of the invention.
Figure 8B:
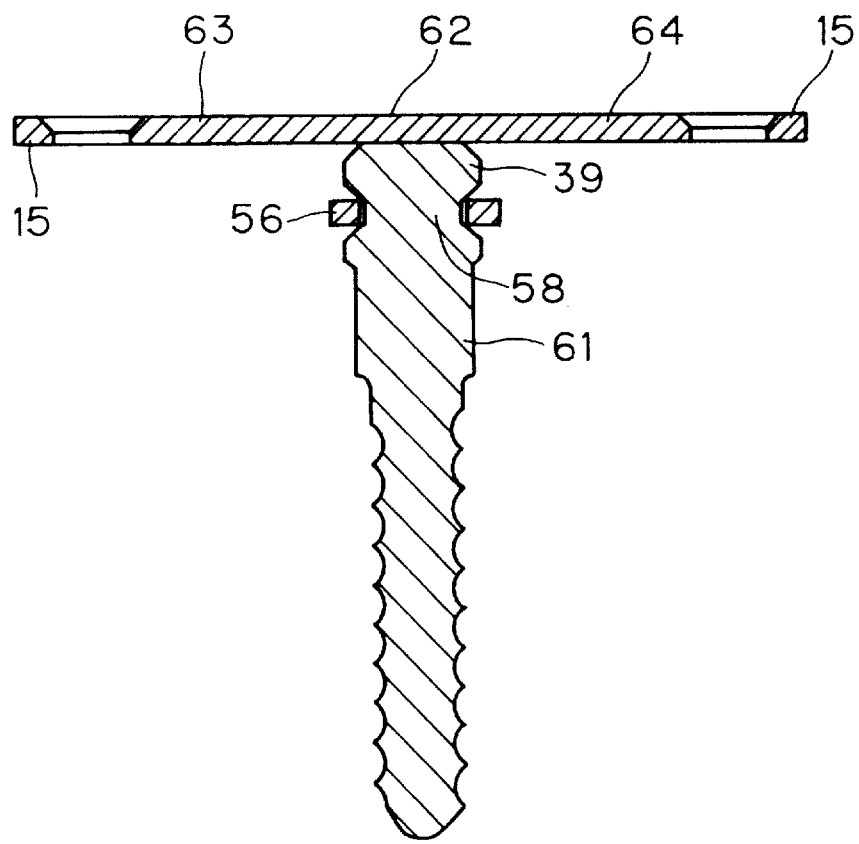
FIG. 8B is a cross-sectional view of the orthodontic supporting structure according to the sixth embodiment taken along line 8B—8B of FIG. 8A.

FIGS. 8A–8B are diagrams showing an orthodontic supporting structure 60 according to a sixth embodiment of the invention, in which FIG. 8A is a top view and FIG. 8B is a cross-sectional view taken along line 8B—8B of FIG. 8A. In FIGS. 8A–8B, elements identical or equivalent to those shown in FIGS. 1A–1B, 2, 5A–5B and 7A–7C are designated by the same reference numerals and a description of such elements is omitted.

A connecting unit 62 of the support 60 of this embodiment has two arms 63, 64 each having a ring-shaped fastening part 15 at a far end.

A narrow part 58 of an implant unit 61 has a hexagonal cross section in top view while an engaging part 56 of the connecting unit 62 has a generally hexagonal inner surface structure opening at one end so that the engaging part 56 can fit on the narrow part 58 as in the fifth embodiment described above.

To attach the connecting unit 62 to the implant unit 61, the engaging part 56 is fitted on the narrow part 58 and far ends 56b of the engaging part 56 are crimped to fix the connecting unit 62 in position as in the foregoing embodiments.

This embodiment makes it possible to provide two supporting points (fastening parts 15) for moving improperly positioned teeth with the single support 60. The two arms 63, 64 of the support 60 need not necessarily be arranged in a straight line (180°) as shown in FIG. 8A but may be arranged in various ways.

Seventh Embodiment

Figure 9:
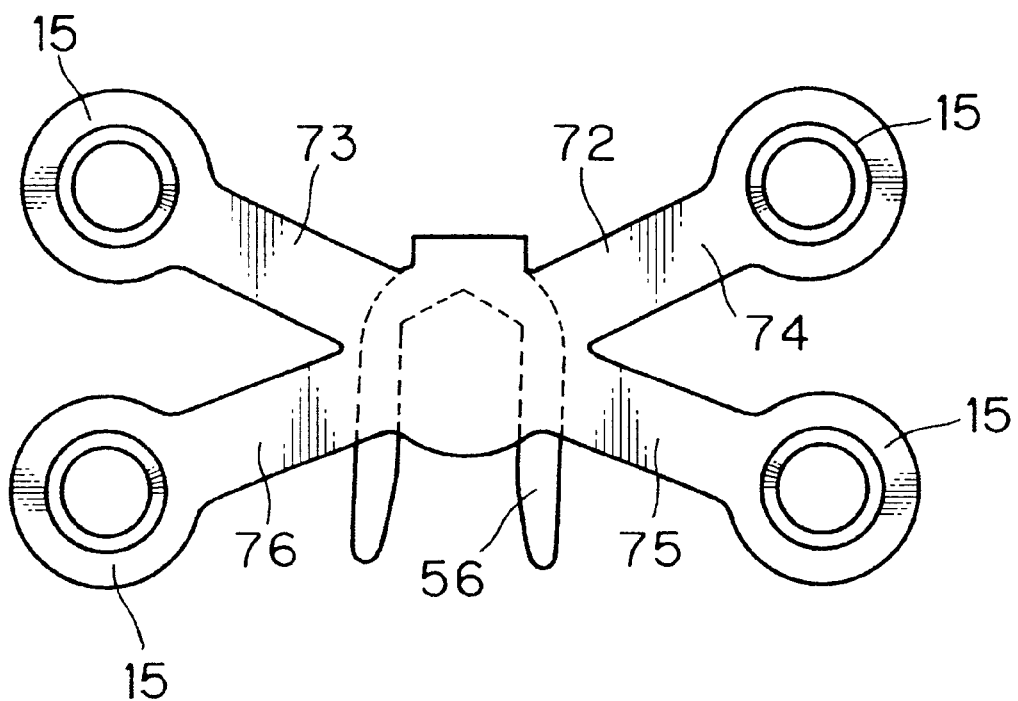
FIG. 9 is a top view of a connecting unit of an orthodontic supporting structure according to a seventh embodiment of the invention.

FIG. 9 is a top view of a connecting unit 72 of an orthodontic supporting structure 70 according to a seventh embodiment of the invention.

The connecting unit 72 of this embodiment has four arms 73, 74, 75, 76 each having a ring-shaped fastening part 15 at a far end. According to the invention, the connecting unit may have three or more arms like this.

With the orthodontic supporting structure having multiple fastening parts as in the sixth and seventh embodiments, it is possible to apply correcting forces to teeth from a plurality of supporting points (fastening parts 15) by implanting the single support.

Eight Embodiment

Figure 10:
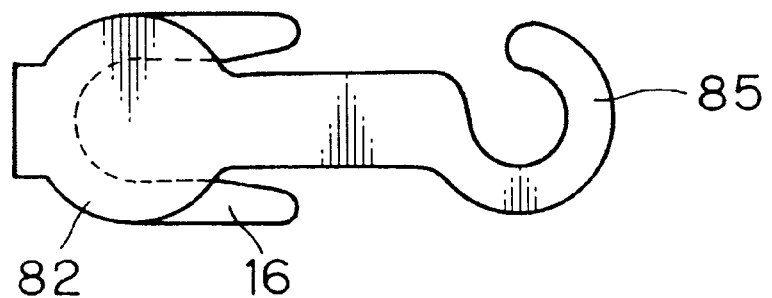
FIG. 10 is a top view of a connecting unit of an orthodontic supporting structure according to an eighth embodiment of the invention.

FIG. 10 is a top view of a connecting unit 82 of an orthodontic supporting structure 80 according to an eighth embodiment of the invention.

The connecting unit 82 of this embodiment has a hooklike fastening part 85 formed at a far end of an arm. The fastening part may be hook-shaped as in the present embodiment or may be shaped like a button formed by swelling, or enlarging, the far end of the arm.

EXAMPLES OF ORTHODONTIC TREATMENT

Practical examples of orthodontic treatment which can be performed using the orthodontic supporting structures of the invention are now described.

First Example of Treatment

Figure 11:
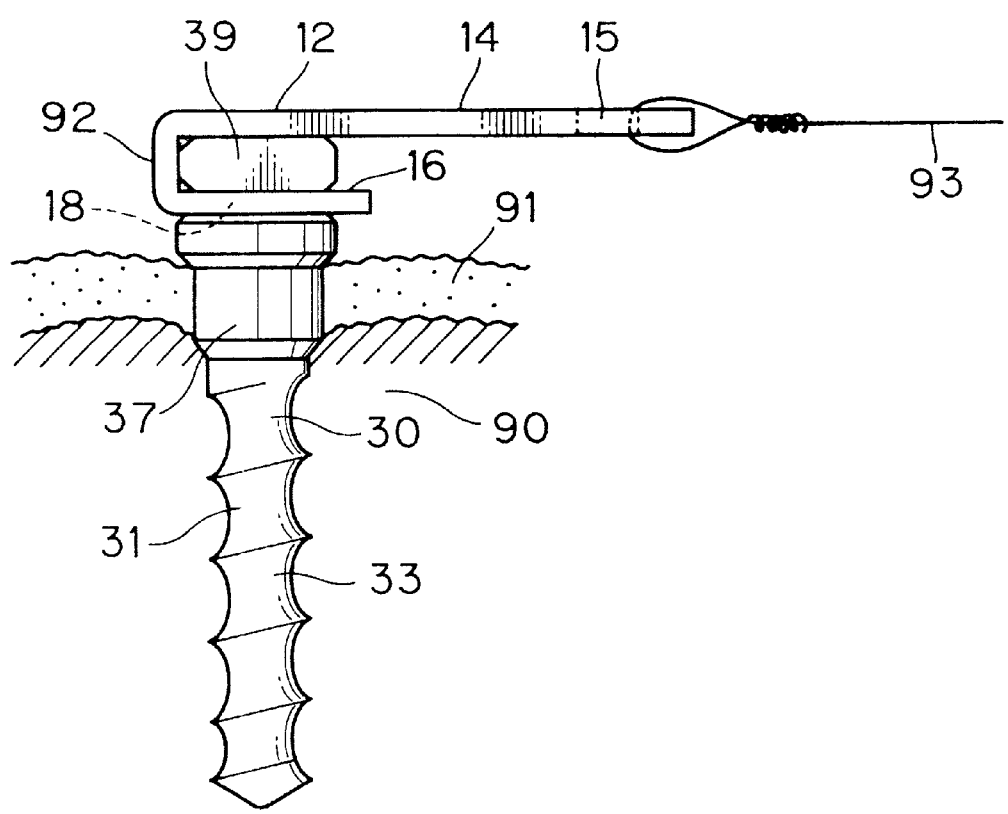
FIG. 11 is a diagram illustrating a first example of treatment using an orthodontic supporting structure of the invention.

FIG. 11 is a diagram illustrating a first example of treatment according to the invention, in which the orthodontic supporting structure 30 is implanted in a jaw bone 90 which is covered with gingival mucosa 91. In FIG. 11, elements identical or equivalent to those shown in FIGS. 1A–1B, 2 and 5A–5B are designated by the same reference numerals and a description of such elements is omitted.

After implanting the implant unit 31 in the jaw bone 90, the connecting unit 12 is fixed to the implant unit 31 in the previously described manner such that the fastening part 15 is located at a desired position. Then, an orthodontist attaches one end of a wire 93 to the fastening part 15 and the other end to a bracket, for instance, which is fixed to a tooth. As a result, a correcting force is applied to the tooth from a proper direction.

According to the invention, the orthodontic supporting structure 30 is located such that its top portion is exposed to the oral cavity and a joint between the implant unit 31 and the connecting unit 12 is situated apart above the gingival mucosa 91 when the support 30 is implanted in the jaw bone 90. It is therefore possible to clean the joint by toothbrushing, for instance, and maintain good cleanliness.

Furthermore, it is possible to remove the support 30 from the jaw bone 90 in an easy and quick manner upon completion of orthodontic treatment since the top portion of the implant unit 31 is exposed to the oral cavity. This can be done by holding the top portion of the implant unit 31 with pliers, for instance, and extracting the implant unit 31. If the top portion of the implant unit 31 exposed to the oral cavity is shaped into a regular hexagon, the implant unit 31 may be removed by turning it with a wrench to undo the externally threaded embedded portion 33 of the implant unit 31. The support 30 can be removed easily and quickly in this case as well.

Preferably, a curved surface 37 below the narrow part 18 of the implant unit 31 should be polished to form a mirror surface. This is because the mirror surface provides good affinity and adhesion to a mucous tissue of the gingival mucosa 91 through which the curved surface 37 passes.

If the connecting unit 12 breaks or the need arises to alter the supporting point (location of the fastening part 15) during the treatment, the connecting unit 12 can be replaced with new one. Moreover, the wire 93 or a lingual chain may be directly attached to the implant unit 31 if it is so desired.

Second Example of Treatment

Figure 12:
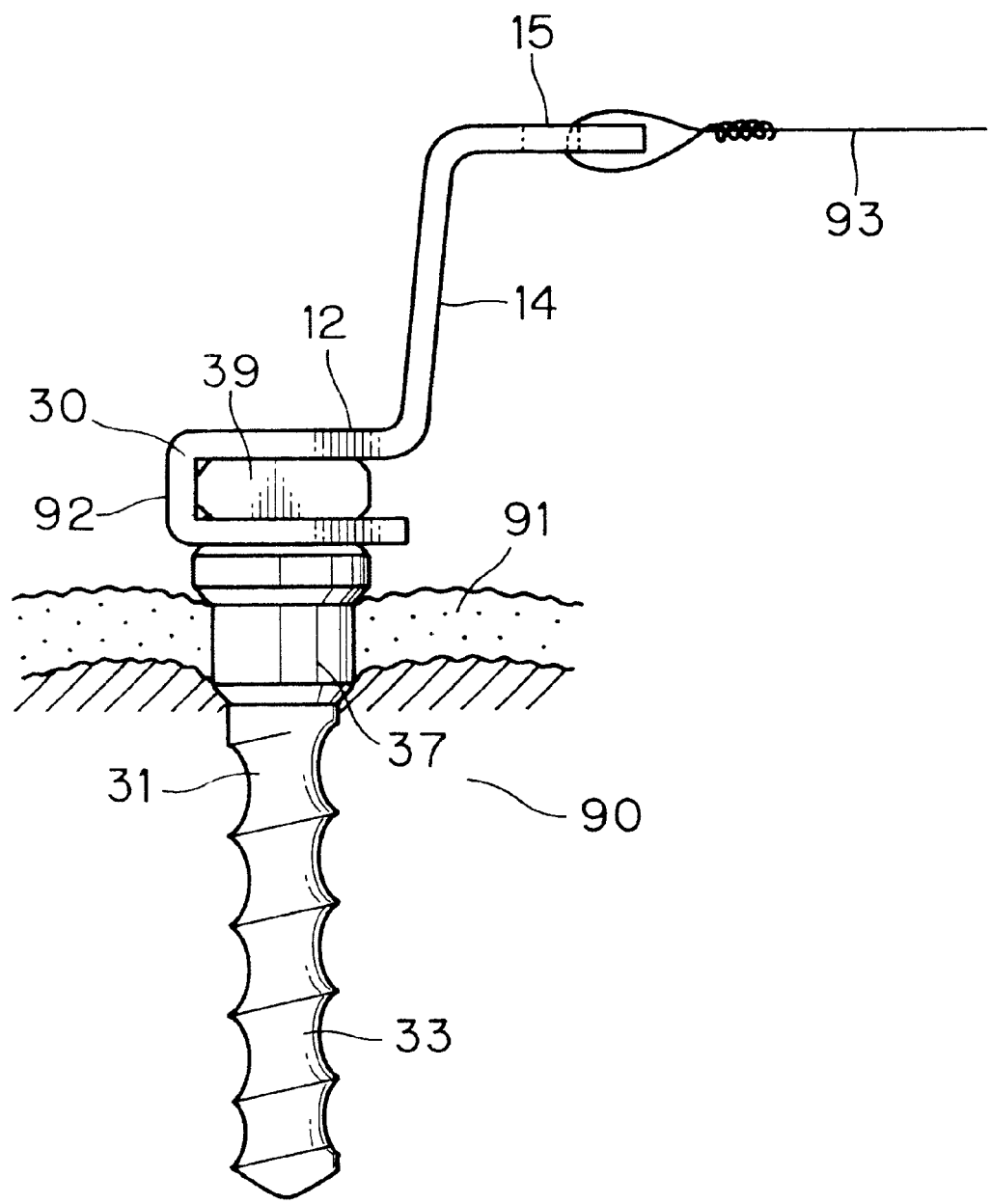
FIG. 12 is a diagram illustrating a second example of treatment using an orthodontic supporting structure of the invention.

FIG. 12 is a diagram illustrating a second example of treatment according to the invention, in which the orthodontic supporting structure 30 is implanted in a jaw bone 90. In FIG. 12, elements identical or equivalent to those shown in FIGS. 1A–1B, 2, 5A–5B and 11 are designated by the same reference numerals and a description of such elements is omitted.

While the arm 14 of the connecting unit 12 extends horizontally in a straight line in the example of FIG. 11, the arm 14 may be bent in an angular or curved shape as shown in FIG. 12. Such bending of the arm 14 is possible if it is made of plastically deformable material.

If a wire 93 or the like attached to the arm 14 or to the fastening part 15 goes in contact with gingival mucosa 91 and causes discomfort or inflammation, or if it is desired to slightly adjust the position of the fastening part 15 (supporting point), it may be set apart from the gingival mucosa 91 or otherwise repositioned by adjusting the bend of the arm 14. In a case where the arm should be bent only in a vertical plane (parallel to the longitudinal axis of the implant unit) and the direction of correcting force lies on a line connecting the tooth to be corrected and the implant unit, the arm need not fixedly extend in a particular horizontal direction. In this case, the embedded portion of the connecting unit and the narrow part of the implant unit may have a circular cross section.

Third Example of Treatment

Figure 13:
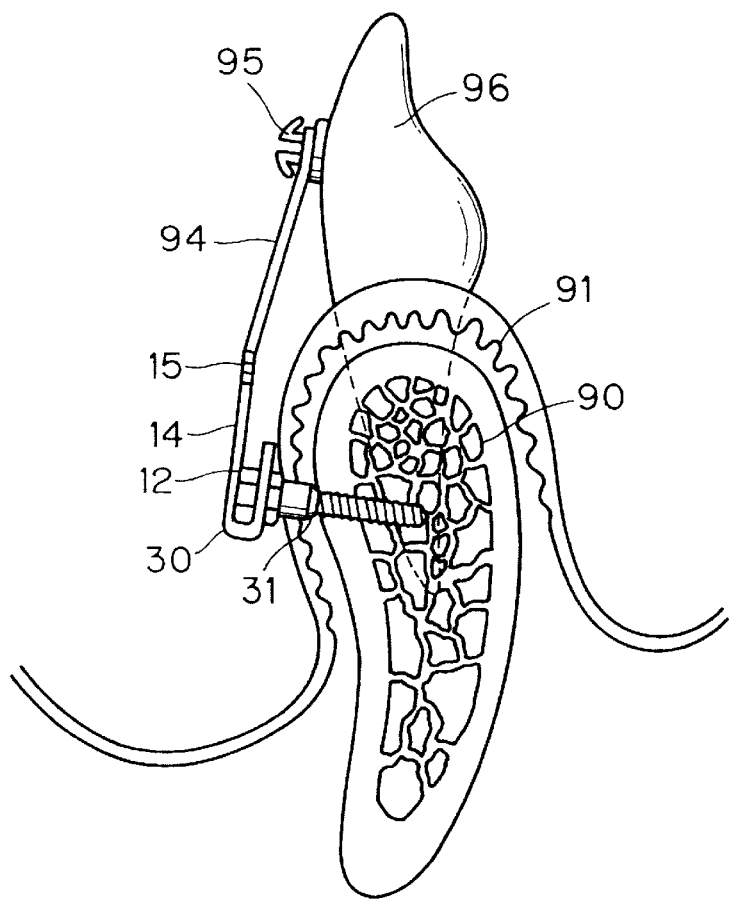
FIG. 13 is a diagram illustrating a third example of treatment using an orthodontic supporting structure of the invention.

FIG. 13 is a diagram illustrating a more practical example of orthodontic treatment which is performed for lowering a canine 96.

The implant unit 31 of the orthodontic supporting structure 30 is implanted in a jaw bone 90 in such a way that the implant unit 31 would not interfere with the root or nerves of the canine 96. Subsequently, the connecting unit 12 is fixed to the implant unit 31 while holding the fastening part 15 at a position where a supporting point is to be located. Then, one end of a rubber chain 94 is attached to the fastening part 15 of the connecting unit 12 and the other end of the rubber chain 94 is fitted to a bracket 95 which is fixed to the canine 96, such that a downward pulling force is applied to the canine 96.

Fourth and Fifth Examples of Treatment

Figure 14:
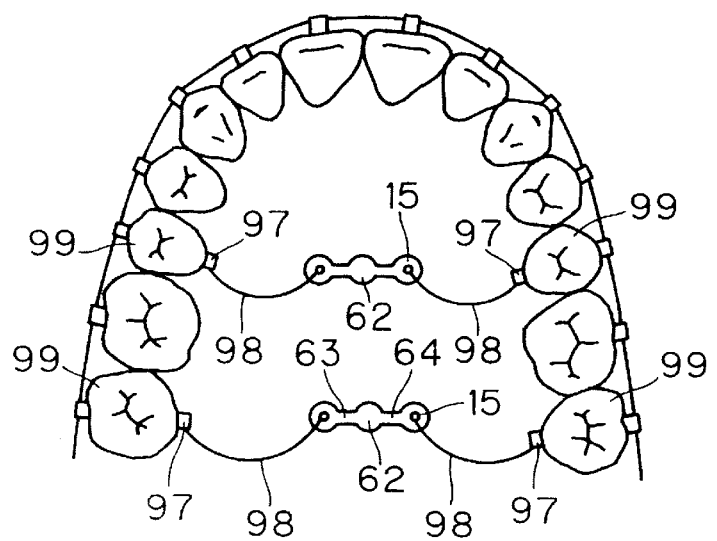
FIG. 14 is a diagram illustrating a fourth example of treatment using two orthodontic supporting structures of the invention.

FIG. 14 is a diagram illustrating a fourth example of treatment according to the invention, in which two pairs of teeth 99 in the upper jaw are corrected using two orthodontic supporting structures. In this example, the orthodontic supporting structures as described in the sixth embodiment (FIGS. 8A–8B) each having two arms 63, 64 are used.

Figure 15:
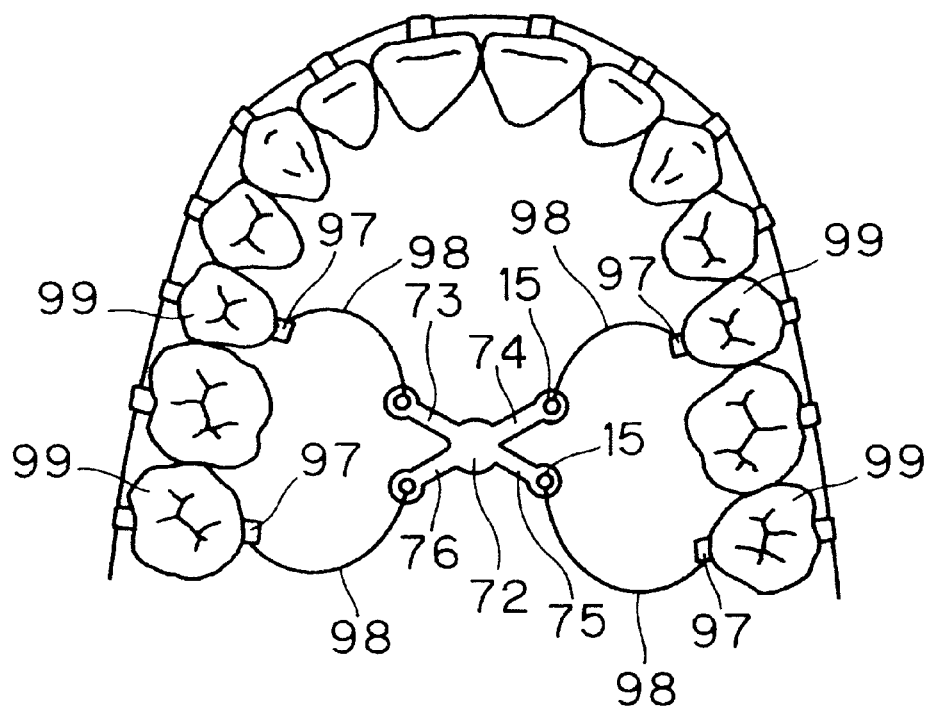
FIG. 15 is a diagram illustrating a fifth example of treatment using an orthodontic supporting structure of the invention.

FIG. 15 is a diagram illustrating a fifth example of treatment according to the invention, in which two pairs of teeth 99 in the upper jaw are corrected using a single orthodontic supporting structure. In this example, the orthodontic supporting structure as described in the seventh embodiment (FIG. 9) having four arms 73–76 is used.

In FIG. 15, leaf springs 98 are fitted to the fastening parts 15 of the individual arms 73–76 of the orthodontic supporting structure implanted in the upper jaw and far ends of the individual leaf springs 98 are attached to lingual buttons 97 which are fixed to the teeth 99. Correcting forces are applied to the multiple teeth 99 in this way to correct their positions.

While the orthodontic supporting structures of the invention have been described referring to the specific examples illustrated in the accompanying drawings, the invention is not limited to those examples. It will be apparent to those skilled in the art that the various changes and modifications are possible in practical applications without departing from the spirit and scope of the invention and all such changes and modifications are included within the technical features of the invention.

As an example, the invention may be modified such that a projection is formed in an inner surface of the engaging part of the connecting unit and a recess which can fit on the projection is formed on the narrow part of the implant unit. In this variation, the connecting unit and the implant unit are fixed more securely as the projection on the engaging part fits into the recess in the narrow part.

Furthermore, although the projections 46c on the engaging part 46 of the fourth embodiment swell in the form of a gentle hill, the projections 46c may be formed into a hooklike shape curving more acutely inward. Such hook-shaped projections would produce greater resistance to a force exerted on the connecting unit in a direction opposite to the direction of arrow A shown in FIG. 6A, so that the engaging part would not come off easily from the implant unit.

Figure 16:
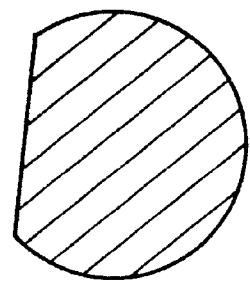
FIG. 16 is a horizontal cross section of a head of an implant unit of an orthodontic supporting structure according to another embodiment of the invention.

FIG. 16 is a horizontal cross section of a head of an implant unit of an orthodontic supporting structure according to another embodiment of the invention. In this embodiment, an intermediate part 92 of a connecting unit has a flat inner surface like the one shown in FIG. 1A and the head of the implant unit has a generally circular cross section with its side cut to form a flat surface as shown in FIG. 16. When the connecting unit is fitted to the implant unit, the flat surface of the implant unit comes in close contact with the flat inner surface of the intermediate part 92 so that the connecting unit is prohibited from turning about the implant unit.

As thus far described, the orthodontic supporting structures of the present invention are easy to handle and the connecting unit can be attached to the implant unit in a simple yet reliable fashion even in the oral cavity which provides a limited treatment space. Accordingly, the orthodontic supporting structures of the invention relieve the orthodontist of excess work load in carrying out orthodontic treatment.

What claimed claims:

1. An orthodontic supporting structure comprising:
   an implant unit which is implantable in a desired site in a jaw bone and defines a longitudinal axis thereof, said implant unit having an upper portion and an upper portion end; and
   a connecting unit attachable to the upper portion of the implant unit, the connecting unit including:
   an arm part having a fastening portion which is extendable over the upper portion end and intersects the longitudinal axis when the connecting unit is attached to the implant unit; and
   an engaging part extending from and beneath the arm part and defining an open-sided aperture for slidably engaging in a radial direction the upper portion of the implant unit by sliding.

2. The orthodontic supporting structure according to claim 1, wherein the implant unit has a narrow part in the upper portion, and the open-sided aperture of the engaging part of the connecting unit has a U-shaped inner surface structure which engages the narrow part of the implant unit.

3. The orthodontic supporting structure according to claim 1, further comprising a locking mechanism provided at a point of contact between the implant unit and the connecting unit to prevent the connecting unit from turning about the implant unit.

4. The orthodontic supporting structure according to claim 1, wherein at least the engaging part of the connecting unit is made of a plastically deformable material and a width of the open-sided aperture in the engaging part is smaller than a maximum thickness of a part of the implant unit where the engaging part is engaged.

5. The orthodontic supporting structure according to claim 1, wherein the arm part is made of a plastically deformable material.

6. The orthodontic supporting structure according to claim 1, wherein the engaging part engages the upper portion of the implant unit in a direction generally perpendicular to a longitudinal axis of the implant unit.

7. The orthodontic supporting structure according to claim 1, wherein the implant unit includes an embedded portion having a maximum diameter equal to or less than 2mm.

8. The orthodontic supporting structure according to claim 1, wherein the implant unit is integral.

9. The orthodontic supporting structure according to claim 1, wherein the engaging part of the connecting unit includes at least one side flap extending downward from the engaging part for engaging the upper portion of the implant unit.

10. The orthodontic supporting structure according to claim 1, wherein the engaging part of the connecting unit includes a pair of opposed far ends which are engageable with the upper portion of the implant unit.

11. The orthodontic supporting structure according to claim 10 wherein the far ends are engageable with the upper portion of the implant unit by crimping.

12. The orthodontic supporting structure according to claim 1, wherein the narrow part has portions defining a groove.

13. The orthodontic supporting structure according to claim 1, wherein the connecting unit further comprises a second fastening portion.

14. The orthodontic supporting structure according to claim 1, wherein the fastening portion is hook-shaped.

15. An orthodontic supporting structure comprising:

an implant unit which is implantable in a desired site in a jaw bone and defines a longitudinal axis thereof, said implant unit having an upper portion, an upper portion end and a narrow part in the upper portion; and a connecting unit attachable to the upper portion of the implant unit, the connecting unit including:

an arm part having a fastening portion which is extendable over the upper portion end and intersects the longitudinal axis when the connecting unit is attached to the implant unit; and an engaging part extending from and beneath the arm part and defining an open-sided aperture for slidably engaging in a radial direction the upper portion of the implant unit by sliding; and a locking mechanism provided at a point of contact between the implant unit and the connecting unit to prevent the connecting unit from turning about the implant unit;

wherein the arm part of the connecting unit and the engaging part thereof, which is shorter than the arm part, are joined by an intermediate part to together form a continuous J-shaped structure, at least one portion of an inner surface of the intermediate part having a flat area, a head of the implant unit has a flat surface provided just above the narrow part of the implant unit and has one of a polygonal cross section, a generally circular cross section, and an elliptical cross section with a side cut to form a flat surface, and the locking mechanism is formed of the flat area on the inner surface of the intermediate part of the connecting unit and the flat surface of the head of the implant unit, and wherein the flat area on the inner surface of the intermediate part comes in contact with the flat surface of the head when the connecting unit is engaged with the implant unit.

16. An orthodontic supporting structure comprising:

an implant unit which is implantable in a desired site in a jaw bone and defines a longitudinal axis thereof, said implant unit having an upper portion, an upper portion end and a narrow part in the upper portion; and a connecting unit attachable to the upper portion of the implant unit, the connecting unit including:

an arm part having a fastening portion which is extendable over the upper portion end and intersects the longitudinal axis when the connecting unit is attached to the implant unit; and an engaging part extending from and beneath the arm part and defining an open-sided aperture for slidably engaging in a radial direction the upper portion of the implant unit by sliding; and a locking mechanism provided at a point of contact between the implant unit and the connecting unit to prevent the connecting unit from turning about the implant unit;

wherein the narrow part of the implant unit has one of a polygonal cross section, an elliptical cross section, and a generally circular cross section with a side cut to form a flat surface, the engaging part of the connecting unit has one of a polygonal inner surface structure, an elliptical inner surface structure, and a generally circular inner surface structure with a side cut to form a flat surface such that the engaging part can fit on the narrow part, and the locking mechanism is formed of the cross-sectional shape of the narrow part and the inner surface structure of the engaging part.

17. An orthodontic supporting structure comprising:

an implant unit which is implantable in a desired site in a jaw bone and defines a longitudinal axis thereof, said implant unit having an upper portion, an upper portion end and a narrow part in the upper portion; and a connecting unit attachable to the upper portion of the implant unit, the connecting unit including:

an arm part having a fastening portion which is extendable over the upper portion end and intersects the longitudinal axis when the connecting unit is attached to the implant unit; and an engaging part extending from and beneath the arm part and defining an open-sided aperture for slidably engaging in a radial direction the upper portion of the implant unit by sliding, said open-sided aperture having a U-shaped inner surface structure which engages the narrow part of the implant unit;

wherein at least the engaging part of the connecting unit is made of a plastically deformable material and the engaging part is fixed to the narrow part of the implant unit by crimping the engaging part.

18. The orthodontic supporting structure comprising:

an implant unit which is implantable in a desired site in a jaw bone and defines a longitudinal axis thereof, said implant unit having an upper portion, an upper portion end and a narrow part in the upper portion; and a connecting unit attachable to the upper portion of the implant unit, the connecting unit including:

an arm part having a fastening portion which is extendable over the upper portion end and intersects the longitudinal axis when the connecting unit is attached to the implant unit; and an engaging part extending from and beneath the arm part and defining an open-sided aperture for slidably engaging in a radial direction the upper portion of the implant unit by sliding, said open-sided aperture having a U-shaped inner surface structure which engages the narrow part of the implant unit;

wherein a head of the implant unit just above the narrow part tapers off toward a longitudinal axis of the implant unit.

* * * * *